(12) United States Patent
Koch et al.

(10) Patent No.: US 9,821,172 B2
(45) Date of Patent: Nov. 21, 2017

(54) THERMOTHERAPY DEVICE

(71) Applicant: Dräger Medical GmbH, Lübeck (DE)

(72) Inventors: Jochim Koch, Ratzeburg (DE); Arne Tröllsch, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 702 days.

(21) Appl. No.: 14/384,231

(22) PCT Filed: Jan. 18, 2013

(86) PCT No.: PCT/EP2013/050885
§ 371 (c)(1),
(2) Date: Sep. 10, 2014

(87) PCT Pub. No.: WO2013/143716
PCT Pub. Date: Oct. 3, 2013

(65) Prior Publication Data
US 2015/0066117 A1   Mar. 5, 2015

(30) Foreign Application Priority Data

Mar. 27, 2012 (DE) .................. 10 2012 006 199
Aug. 17, 2012 (DE) .................. 10 2012 214 678

(51) Int. Cl.
*A61N 5/06* (2006.01)
*A61G 11/00* (2006.01)
(Continued)

(52) U.S. Cl.
CPC .............. *A61N 5/0625* (2013.01); *A61F 7/00* (2013.01); *A61G 11/00* (2013.01); *A61G 11/002* (2013.01);
(Continued)

(58) Field of Classification Search
CPC combination set(s) only.
See application file for complete search history.

(56) References Cited

U.S. PATENT DOCUMENTS 6,245,010 B1   6/2001  Jones
2009/0177257 A1*  7/2009  Khodak .................. A61G 11/00
                                                            607/96

FOREIGN PATENT DOCUMENTS

EP   0 872 227 A2   10/1998
EP   2 172 175 A2   4/2010
WO   2009/088607 A1   7/2009

* cited by examiner

*Primary Examiner* — Joseph Stoklosa
*Assistant Examiner* — Adam Avigan
(74) *Attorney, Agent, or Firm* — McGlew and Tuttle, P.C.

(57) ABSTRACT

A thermotherapy device for treatment of neonates has a bordered lying surface (5) for receiving a neonate, a vertical support column (8) arranged adjacent to the head end of the lying surface (5) and radiant heaters (3, 4), supported by the column, directed at the lying surface (5). A control unit controls the heating output of each of the radiant heaters (3, 4). At least one first radiant heater (4) is directed at a head end half of the lying surface (5). At least one second radiant heater (3) is directed at the other half of the lying surface. The control unit (9) adjusts the heating output of the first radiant heater and the second radiant heater in such that, with the lying surface (5) arranged horizontally, the heating output of the second radiant heater (3) is greater by a predefined factor than that of the first radiant heater (4).

18 Claims, 4 Drawing Sheets

(51) Int. Cl.
*A61F 7/00* (2006.01)
*A61B 90/00* (2016.01)

(52) U.S. Cl.
CPC ... *A61B 2090/061* (2016.02); *A61B 2090/067* (2016.02); *A61F 2007/0088* (2013.01); *A61F 2007/0093* (2013.01); *A61G 11/008* (2013.01); *A61G 2200/14* (2013.01); *A61G 2203/30* (2013.01); *A61G 2203/42* (2013.01); *A61N 2005/0626* (2013.01); *A61N 2005/0639* (2013.01); *A61N 2005/0659* (2013.01)

THERMOTHERAPY DEVICE

CROSS REFERENCE TO RELATED APPLICATIONS

This application is a U.S. National Phase Application of International Application PCT/EP2013/050885 filed Jan. 18, 2013 and claims the benefit of priority under 35 U.S.C. §119 of German Patent Applications DE 10 2012 006 199.4 filed Mar. 27, 2012 and DE 10 2012 214 678.4 filed Aug. 17, 2012, the entire contents of which are incorporated herein by reference.

FIELD OF THE INVENTION

The invention pertains to a thermotherapy device (heat therapy appliance) for the treatment of newborns with a bordered reclining surface for accommodating a newborn and with a vertical support column, which is arranged adjacent to the head end of the reclining surface and at which a plurality of heating radiators directed at the bordered reclining surface are suspended, and with a control unit, which is set up to control the heat outputs of the plurality of heating radiators.

BACKGROUND OF THE INVENTION

Such a thermotherapy device is known, for example, from WO 2009/088607 A1. Adjoining the head end of the reclining surface is located a vertical support column, which carries at its upper end a plurality of heating radiators, which are arranged in a matrix. A control unit detects the temperature as a function of the location on the reclining surface with a plurality of temperature sensors. The heating radiator matrix is then controlled by the control unit such that the patient will receive a uniform temperature along his entire body. Areas of the reclining surface that are not occupied by the patient are detected by temperature sensors and the heating elements associated with them are deactivated. However, this device is complicated because of the plurality of temperature sensors.

It is generally problematic for designing the radiant heater that this shall be arranged vertically above the head end of the reclining surface in order to make place for an upwardly pivotable hood or for an X-ray apparatus. The hood is movable between a closed position covering the reclining surface and an opened position, in which it lies outside the radiation cone from the radiant heater to the reclining surface. However, a non-uniform heat output is obtained on the reclining surface in case of an individual heating radiator suspended on a support column above the head end, because the incidence angle varies from the head end to the foot end of the reclining surface and, moreover, the distance between heating radiators and the reclining surface increases from the head end to the foot end of the reclining surface.

In the thermotherapy device that is described in U.S. Pat. No. 6,245,010 B1, a symmetrical heating radiator is suspended on a support column located at the head end and is directed at the reclining surface. A temperature difference of 3.2° C. arises in such an arrangement on the reclining surface because of the variations from the head end to the foot end if the measurements carried out with test bodies according to IEC 60601-2-21.

The thermotherapy device described in EP 2 172 175 A2 is likewise provided with an individual heating radiator on a support column, and these heating radiators have an asymmetrical reflector, which shall compensate the variation of the incidence angle and distance from the head end to the foot end of the reclining surface. It was, however, found that a relatively great temperature difference still remains between the head end and the foot end, which is about 1.6° C. if the measurements are made with test bodies according to IEC 60601-2-21.

The best devices in use, which have the radiant heater directed above and in parallel to the reclining surface, reach a temperature difference of about 0.8° C. under the same conditions. However, such an arrangement cannot be embodied for thermotherapy devices that have a pivotable hood at the support column, which hood is movable between a closed position for the incubator operation and a position for open nursing care, in which position the path of the radiation towards the reclining surface is released.

SUMMARY OF THE INVENTION

An object of the present invention is therefore to design a thermotherapy device such that it achieves the most uniform temperature regulation possible from the head end to the foot end of the reclining surface despite the fact that the heating radiators are arranged at the head end.

According to the present invention, a thermotherapy device is provided for treating newborns. The thermotherapy device comprises a bordered reclining surface for accommodating a newborn and with a vertical support column, which is arranged adjacent to the head end of the reclining surface. The vertical support column supports a plurality of heating radiators directed at the bordered reclining surface are fixed, and with a control unit, which is set up to control the heat outputs of the plurality of heating radiators at least one first heating radiator is directed at the half of the reclining surface located at the head end of the reclining surface. At least one second heating radiator is directed at the half of the reclining surface located at the foot end. The control unit is set up to set the heat outputs of the first heating radiator and of the second heating radiator, with the reclining surface in a horizontal position, such that the heat output of the second heating radiator is greater than that of the first heating radiator by a preset factor.

A heating radiator is defined in connection with the present invention as a heater in the form of a high-temperature radiator, which releases heat predominantly by heat radiation. A heating coil, through which electric current flows, or, in connection with the present invention, preferably a current-carrying heating rod is heated in a high-temperature radiator, and it radiates heat as a result in the form of infrared rays. The heating rod is partially enclosed by a reflector, which focuses the infrared rays in a preferred direction.

The phrase that a heating radiator is directed at a desired half of the reclining surface means that the heating radiator focuses the infrared radiation such that the maximum power density is located in the plane of the reclining surface in the desired half of the reclining surface. The power density of the infrared radiation is defined as the irradiated power per unit area in the plane of the reclining surface and corresponds to the intensity. The directedness of the heating radiator toward a half of the reclining surface also means that the power density integrated over this half of the reclining surface is greater than the power density of the heating radiator integrated over the other half of the reclining surface.

When referring to a first heating radiator and a second heating radiator in connection with the invention, this does not mean that two separate assembly units must be present.

A first heating rod and a second heating rod, which are supplied with current separately, may rather also be integrated in one assembly unit, and the reflectors of the first heating radiator and of the second heating radiator may in this case be integrated in one component.

The preset factor is selected in an advantageous embodiment such that with the reclining surface directed horizontally, the variation of the power density of the heating radiation over the reclining surface is minimized.

Provisions are made in an advantageous embodiment for the first heating radiator to be adapted to focus the heating radiation onto the reclining surface such that the power density of the first heating radiator increases from the foot end to the head end, and for the second heating radiator to be adapted to focus the heating radiation onto the reclining surface such that the power density of the second heating radiator increases from the head end to the foot end. These opposite gradients of the power densities of the two heating radiators can be embodied by a mirror-symmetrically opposite asymmetrical shape of the reflectors such that the variation of the added power densities of the first heating radiator and the second heating radiator is minimized over the reclining surface.

It is often desirable in open nursing care to position the reclining surface with the infant obliquely in order to keep the airways free and to lower the blood pressure in the brain. In an advantageous embodiment, the control unit is set up, further, to detect an oblique position of the reclining surface in relation to the horizontal planes by means of sensors and to adapt the ratio of the heat output of the first heating radiator to the heat output of the second heating radiator in a preset function on the angle of the oblique position such that the variation of the intensity of the heating radiation over the reclining surface is minimized.

Furthermore, provisions may also be made in open nursing care for moving the reclining surface upward relative to the side walls surrounding the reclining surface in order to obtain better access to the infant thereby. In another embodiment, the control unit is set up, further, to detect a vertical adjustment of the reclining surface by means of sensors and to adapt the heat output of the first heating radiator and of the second heating radiator in a preset function on the adjusted height such that a previously set heat output intensity distribution remains essentially unchanged over the reclining surface.

The first heating radiator may be directed centered toward the half of the reclining surface located at the head end of the reclining surface and the second heating radiator may be directed centered toward the other half of the reclining surface. It was, however, found that it is advantageous not to direct the respective heating radiators centered exactly at their respective halves, but somewhat farther apart from one another in order to prevent an excessively high heat output in the middle of the reclining surface because of the superimposition of the radiation cones of the two heating radiators.

Exactly two heating radiators are preferably used. However, it is, of course, also possible to provide three or more heating radiators.

The present invention will be described below on the basis of exemplary embodiments in connection with the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
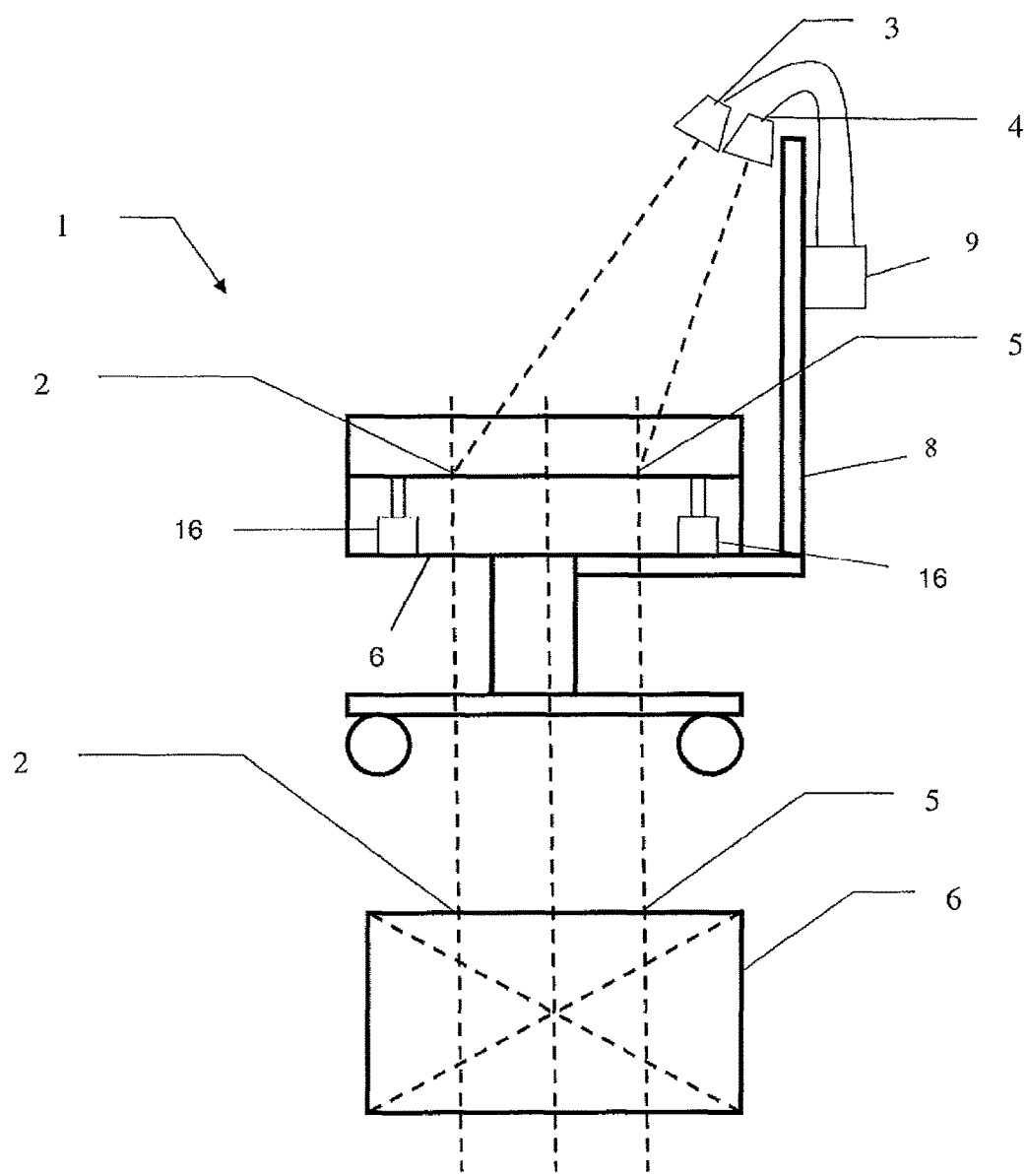
FIG. 1 is a schematic side view of the thermotherapy device.

Referring to the drawings in particular, the thermotherapy device 1 shown in FIG. 1 has a bordered reclining surface, at the head end of which a vertical support column 8 is arranged. The vertical support column 8 carries a first heating radiator 4 and a second heating radiator 3 vertically above the area of the head end. The first heating radiator 4 is directed with the central line at the center 5 of the half of the reclining surface that is located at the head end. The second heating radiator 3 is directed at the center 2 of the remaining other half of the reclining surface 6. A control unit 9 is connected with the first heating radiator 4 and with the second heating radiator 3 in order to set the heat output thereof. The control unit 9 is set up to operate the second heating radiator 3 with full output (100%) when the reclining surface is positioned horizontally, while the first heating radiator 4 is operated cyclically by the control unit 9 with a reduced output of about 80%. The larger mean incidence angle and the short distance between the first heating means 4 and the reclining surface are compensated in this manner. If the necessary total output of the heating radiators 3, 4 is lower, both radiators are adjusted to lower output at an equal ratio of 8:10.

Lifting means 16, which are controlled by the control unit, act on the reclining surface 6. By actuating the lifting means 16 in the same direction and by the same amount, the vertical adjustment of the reclining surface 6 can be set relative to the side walls surrounding same. As a result, the reclining surface 6 can be raised, e.g., relative to the side walls in order to achieve better accessibility thereby to the infant on the reclining surface. The control unit 9 can be set up to adapt the heat outputs of the first and second heating radiators 4 and 3 as a function of the vertical adjustment of the reclining surface, so that the intensity is maintained at a constant value on the reclining surface.

Figure 2:
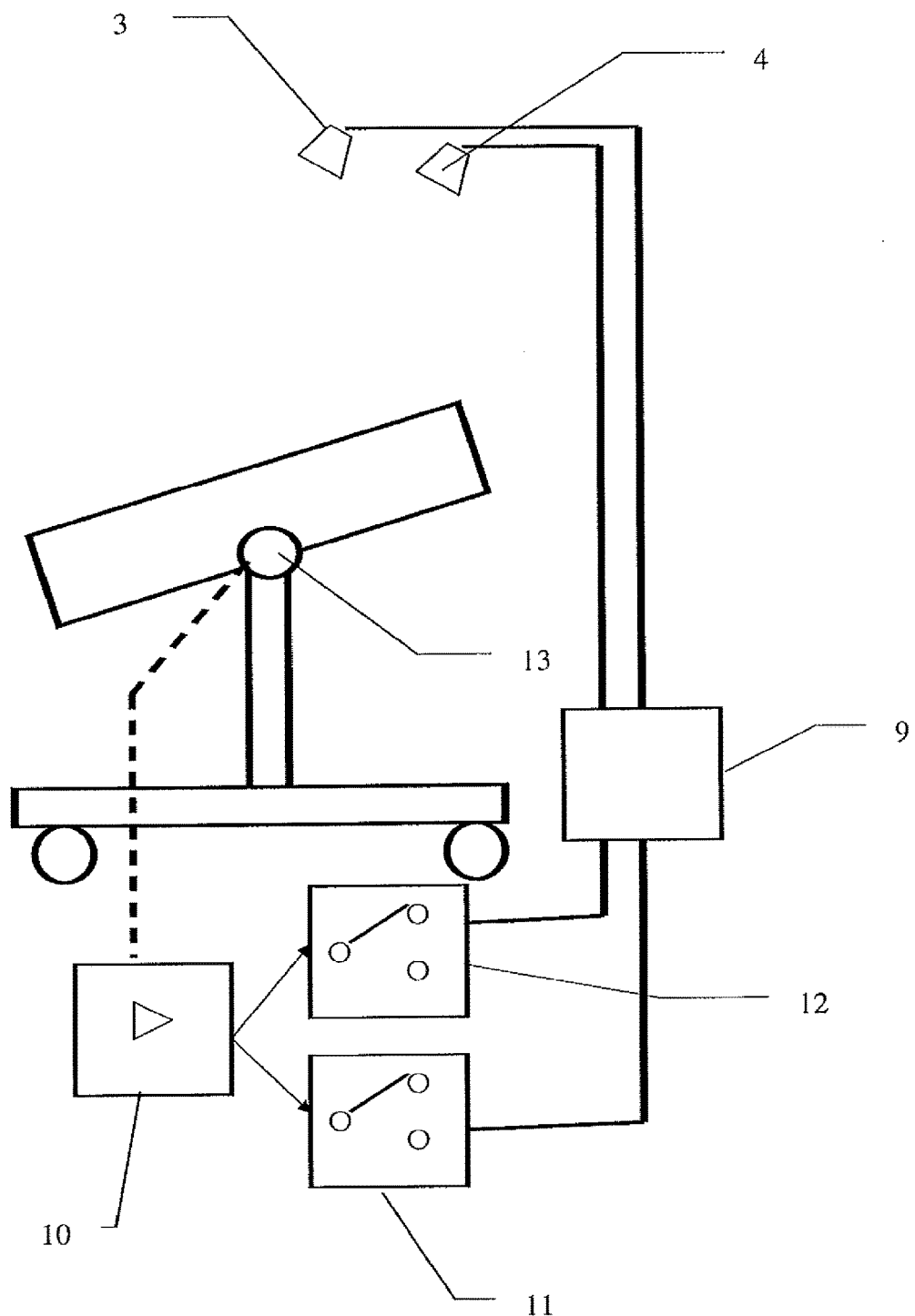
FIG. 2 is a schematic side view of a thermotherapy device with obliquely positioned reclining surface.

The thermotherapy device shown in FIG. 2 has no lifting means for setting the vertical position of the reclining surface, but it offers the possibility of positioning the reclining surface obliquely by pivoting about an axis 13, for example, to position the head end of the reclining surface higher, as is shown. The head end of the reclining surface comes even closer to the first heating radiator 4 in this case, so that the heat output of the first heating radiator 4 can be set lower relative to the heat output of the second heating radiator 3, for example, at the ratio of 7:10. A sensor 10, which detects the degree of oblique position of the reclining surface, is provided in the exemplary embodiment being shown. The control unit 9 is set up to adapt the ratio of the heat outputs of the first and second heating radiators 4, 3 by means of control signal generators 11 and 12 depending on the detected degree of the oblique position of the reclining surface such that the variations of the heat output over the reclining surface are minimized.

The adjustability of the vertical position of the reclining surface, as is shown in FIG. 1, and the pivotability of the reclining surface, as is shown in FIG. 2, may, of course also be combined with one another.

Figure 3:
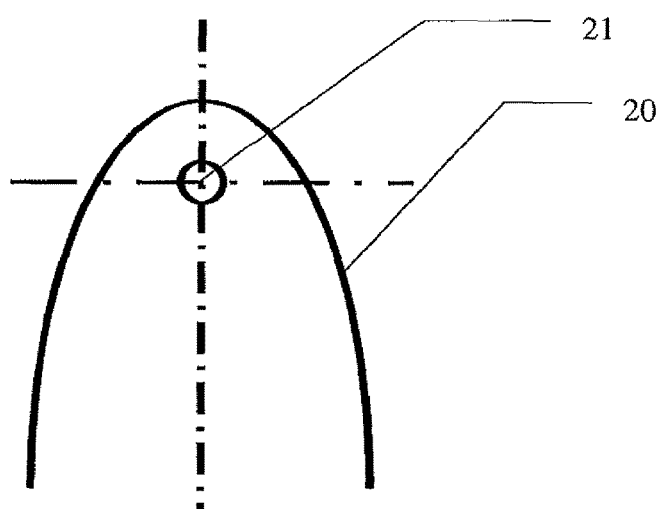
FIG. 3 is a sectional view of a heating radiator with a symmetrical, parabolic reflector.
Figure 4:
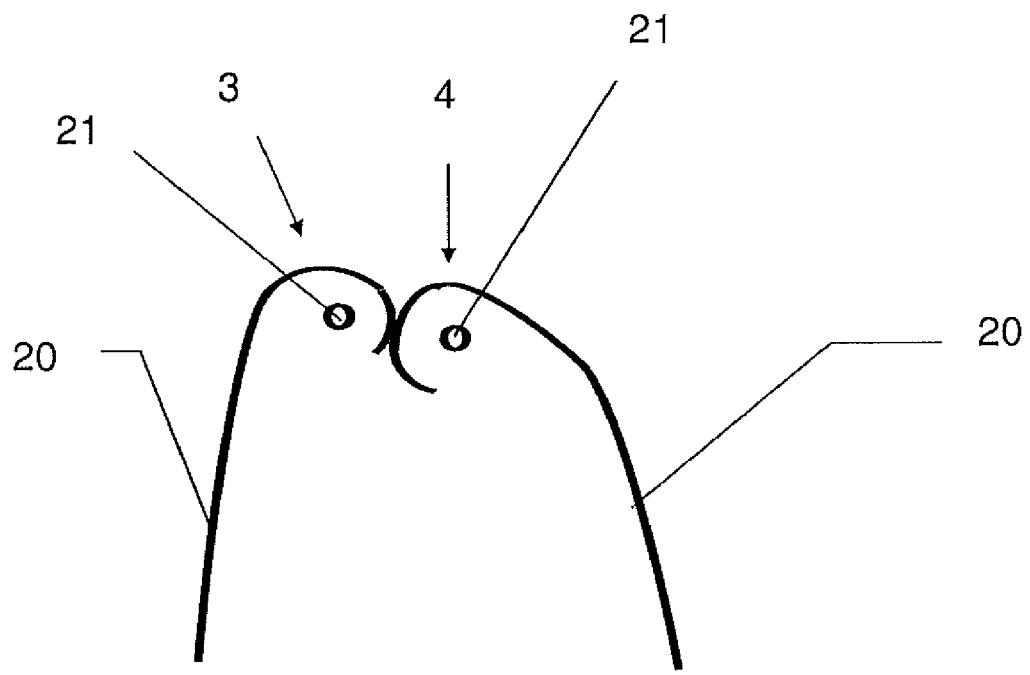
FIG. 4 is a sectional view of a heating radiator with two intermeshing spiral reflectors.

FIG. 3 shows a sectional view of a heating radiator, whose heating rod 21 is aligned with the central axis. The reflector 20 has a symmetrical, parabolic shape, whose focus is located in the axis of the heating rod. However, it is preferred according to the present invention to use asymmetrical reflectors, which are adapted to generate a gradient of the radiation density from the head end to the foot end. Reflector shapes that have a spiral cross section and enclose the heating rod on one side at a relatively short distance and have an increasing distance from it on the way to the other side are suitable for this. A schematic example is shown in the sectional view in FIG. 4. The heating radiators 3, 4 have a reflector 20 each with opposite asymmetry, i.e., they enclose the corresponding heating rod 21 on the side that faces the other heating radiator at a shorter distance and with a greater curvature, while the distance increases on the way towards the other side and the curvature decreases.

While specific embodiments of the invention have been shown and described in detail to illustrate the application of the principles of the invention, it will be understood that the invention may be embodied otherwise without departing from such principles.

The invention claimed is:

1. A thermotherapy device for treating newborns, the thermotherapy device comprising:
    a bordered reclining surface for accommodating a newborn;
    a vertical support column arranged adjacent to a head end of the reclining surface;
    a sensor that detects a degree of obligue position of the reclining surface;
    a plurality of heating radiators, directed at the bordered reclining surface, fixed to the vertical support column; and
    a control unit, which is set up to control the heat outputs of the plurality of heating radiators based at least on an angular position of the reclining surface detected by the sensor, wherein the plurality of heating radiators comprise at least one first heating radiator directed at the half of the reclining surface located at the head end of the reclining surface and at least one second heating radiator directed at the half of the reclining surface located at the foot end, and the control unit is further set up to adjust the heat outputs of the first heating radiator and of the second heating radiator such that with the reclining surface positioned horizontally, the heat output of the second heating radiator is greater by a preset factor than that of the first heating radiator.

2. A thermotherapy device in accordance with claim 1, wherein the preset factor is selected to be such that the variation of an intensity of the heat radiation over the reclining surface is minimized.

3. A thermotherapy device in accordance with claim 2, wherein the first heating radiator is adapted to focus the heat radiation onto the reclining surface such that the power density increases from the foot end to the head end and such that the second heating radiator is adapted to focus the heat radiation to the reclining surface such that the power density increases from the head end to the foot end, so that the variation of the added power densities of the first and second heating radiators over the reclining surface is minimized.

4. A thermotherapy device in accordance with claim 1, wherein the sensors is one of a plurality of sensors to sense an oblique position of the reclining surface, wherein the control unit detects an oblique position of the reclining surface relative to a horizontal plane by means of the sensors and adapts the ratio of the heat output of the first heating radiator to the heat output of the second heating radiator in a preset function on the angle of the oblique position such that the variation of the intensity of the heat radiation over the reclining surface is minimized.

5. A thermotherapy device in accordance with claim 1, further comprising lifting means acting on the reclining surface wherein the control unit is set up to make the reclining surface upwardly displaceable relative to side walls surrounding the reclining surface by actuating the lifting means in order to achieve better access to the infant thereby, and to make it again downwardly displaceable.

6. A thermotherapy device in accordance with claim 5, wherein the sensors comprises one or more sensors for detecting a vertical adjustment of the reclining surface wherein the control unit is set up, further, to detect the vertical adjustment of the reclining surface by means of the one or more sensors and to adapt the heat output of the first heating radiator and of the second heating radiator in a preset function of the vertical adjustment such that a previously set intensity distribution of the heat output remains essentially unchanged over the reclining surface.

7. A thermotherapy device for treating newborns, the thermotherapy device comprising:
    a reclining surface for accommodating a newborn;
    a wall structure bordering the reclining surface;
    a support column arranged adjacent to a head end of the reclining surface;
    a first heating radiator directed at a head end half of the reclining surface, the first heating radiator being supported by the support column;
    a second heating radiator directed at a foot end half of the reclining surface, the second heating radiator being supported by the support column;
    a sensor that detects a degree of oblique position of the reclining surface;
    a control unit configured to control a heat output of the first heating radiator and to control a heat output of the second heating radiator based at least partially on the detected degree of oblique position of the reclining surface detected by the sensor and such that with the reclining surface positioned horizontally, the heat output of the second heating radiator is greater by a preset factor than that of the first heating radiator.

8. A thermotherapy device in accordance with claim 7, wherein the preset factor minimizes a variation of an intensity of heat radiation over the reclining surface.

9. A thermotherapy device in accordance with claim 8, wherein:
    the first heating radiator is configured to direct the heat radiation onto the reclining surface such that a first heating radiator heat radiation power density increases from a foot end toward a head end; and
    the second heating radiator is configured to direct the heat radiation to the reclining surface such that a second heating radiator power density increases from the head end to the foot end such that a variation of a combined heat radiation power density of the first heating radiator and the second heating radiator, over the reclining surface, is minimized.

10. A thermotherapy device in accordance with claim 7, wherein the sensor is part of a sensor arrangement sensing an angular position of the reclining surface, wherein:
- the control unit is configured to detect the angular position deviation from horizontal based on a sensing by the a sensor arrangement; and
- the control unit is configured to control a heat output of the first heating radiator and to control a heat output of the second heating radiator to set a ratio of the heat output of the first heating radiator to the heat output of the second heating radiator that is a preset function of the angular position deviation from horizontal such that a variation of an intensity of heat radiation over the reclining surface is minimized.

11. A thermotherapy device in accordance with claim 7, further comprising a height adjusting structure acting on the reclining surface, wherein the control unit controls the height adjusting structure for displacing the reclining surface relative to the wall structure to change access to the infant.

12. A thermotherapy device in accordance with claim 11, wherein the sensor is part of a sensor arrangement for sensing a vertical adjustment of the reclining surface wherein the control unit is configured to detect a vertical adjustment of the reclining surface based on the sensing by the sensor arrangement and to adapt the heat output of the first heating radiator and of the second heating radiator in a preset function of the vertical adjustment such that a previously set intensity distribution of the heat output remains essentially unchanged over the reclining surface.

13. A thermotherapy device for treating newborns, the thermotherapy device comprising:
- a reclining surface for accommodating a newborn;
- a wall structure bordering the reclining surface;
- a support column arranged adjacent to a head end of the reclining surface;
- a first heating radiator directed at a head end half of the reclining surface, the first heating radiator being supported by the support column at a first heating radiator distance from the head end half of the reclining surface;
- a second heating radiator directed at a foot end half of the reclining surface, the second heating radiator being supported by the support column at a second heating radiator distance from the foot end half of the reclining surface;
- a sensor arrangement comprising one or more sensor, the sensor arrangement detecting an angular position of the reclining surface;
- a control unit configured to control a heat output of the first heating radiator and to control a heat output of the second heating radiator based on the angular position of the reclining surface detected by the sensor arrangement and such that the heat output of the second heating radiator is greater by a preset factor than the heat output of the first heating radiator, the preset factor corresponding to a relationship between the second heating radiator distance and the first heating radiator distance with the reclining surface in a horizontal position.

14. A thermotherapy device in accordance with claim 13, wherein the preset factor minimizes a variation of an intensity of heat radiation over the reclining surface.

15. A thermotherapy device in accordance with claim 13, wherein:
- the first heating radiator is configured to direct the heat radiation onto the reclining surface such that a first heating radiator heat radiation power density increases from a foot end toward a head end; and
- the second heating radiator is configured to direct the heat radiation to the reclining surface such that a second heating radiator power density increases from the head end to the foot end such that a variation of a combined heat radiation power density of the first heating radiator and the second heating radiator, over the reclining surface, is minimized.

16. A thermotherapy device in accordance with claim 13, wherein:
- the control unit is configured to detect the angular position changes with respect to the reclining surface in the horizontal position, based on a sensing by the sensor arrangement;
- the control unit is configured to change the preset factor with angular position changes, with the changed preset factor corresponding to a change in the relationship between the second heating radiator distance and the first heating radiator distance;
- the control unit is configured to control a heat output of the first heating radiator and to control a heat output of the second heating radiator based on the changed preset factor whereby a ratio of the heat output of the first heating radiator to the heat output of the second heating radiator is a function of the angular position of the reclining surface, such that a variation of an intensity of heat radiation over the reclining surface is minimized.

17. A thermotherapy device in accordance with claim 16, a height adjusting structure acting on the reclining surface, wherein the control unit controls the height adjusting structure for displacing the reclining surface relative to the wall structure to change access to the infant.

18. A thermotherapy device in accordance with claim 17, wherein the sensor arrangement is further for sensing a vertical adjustment of the reclining surface wherein the control unit is configured to detect a vertical adjustment of the reclining surface based on the sensing by the sensor arrangement and to adapt the heat output of the first heating radiator and of the second heating radiator in a preset function of the vertical adjustment such that a previously set intensity distribution of the heat output remains essentially unchanged over the reclining surface.

* * * * *